(12) United States Patent
Nishijima et al.

(10) Patent No.: US 9,074,975 B2
(45) Date of Patent: Jul. 7, 2015

(54) PARTICULATE MATTER DETECTING APPARATUS

(75) Inventors: Hiroki Nishijima, Suntou-gun (JP); Keiichiro Aoki, Suntou-gun (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 233 days.

(21) Appl. No.: 13/521,099

(22) PCT Filed: Jan. 27, 2011

(86) PCT No.: PCT/IB2011/000135
§ 371 (c)(1),
(2), (4) Date: Jul. 9, 2012

(87) PCT Pub. No.: WO2011/092582
PCT Pub. Date: Aug. 4, 2011

(65) Prior Publication Data
US 2013/0008231 A1   Jan. 10, 2013

(30) Foreign Application Priority Data
Jan. 29, 2010   (JP) ................................. 2010-018629

(51) Int. Cl.
*G01N 15/06*   (2006.01)

(52) U.S. Cl.
CPC ................... *G01N 15/0656* (2013.01)

(58) Field of Classification Search
CPC ............ G01N 27/4067; G01N 27/406; G01N 27/407; G01N 2015/0053; G01N 15/0656; G01N 27/00–27/99
USPC .............................................. 205/775–794.5
See application file for complete search history.

(56) References Cited

U.S. PATENT DOCUMENTS

| | | | |
|---|---|---|---|
| 4,814,045 A * | 3/1989 | Ohsuga et al. | 205/784.5 |
| 2009/0217737 A1 | 9/2009 | Dorfmueller et al. | |

FOREIGN PATENT DOCUMENTS

| | | |
|---|---|---|
| DE | 101 56 946 A1 | 5/2003 |
| JP | 2005510710 W * | 4/2005 |

(Continued)

OTHER PUBLICATIONS

May 15, 2012 Office Action issued in Japanese Patent Application No. 2010-018629 (with partial translation).

(Continued)

*Primary Examiner* — Harry D Wilkins, III
*Assistant Examiner* — Ciel Thomas
(74) *Attorney, Agent, or Firm* — Oliff PLC

(57) ABSTRACT

A particulate matter detecting apparatus that measures an amount of particulate matter in a gas by applying a predetermined voltage between a pair of first electrodes of a sensor element portion includes a detecting portion that detects whether more particulate matter than a reference amount has accumulated on the first electrodes, a temperature controlling portion that controls a temperature of the sensor element portion to become equal to or higher than a reference temperature when it is detected that more particulate matter than the reference amount has accumulated, and a voltage controlling portion that applies a reference voltage between the first electrodes and a second electrode arranged such that a solid electrolyte is sandwiched between the second electrode and the first electrodes, when it is detected that more particulate matter than the reference amount has accumulated.

3 Claims, 5 Drawing Sheets

(56) References Cited

FOREIGN PATENT DOCUMENTS

| | | | |
|---|---|---|---|
| JP | A-2006-515066 | 5/2006 | |
| JP | A-2006-200520 | 8/2006 | |
| JP | A-2008-547032 | 12/2008 | |
| JP | A-2009-144512 | 7/2009 | |
| JP | A-2009-281974 | 12/2009 | |
| JP | A-2010-261782 | 11/2010 | |
| WO | WO 2008138849 A1 * | 11/2008 | ............. G01N 15/06 |

OTHER PUBLICATIONS

Nov. 9, 2011 Office Action issued in Japanese Patent Application No. 2010-018629 (with partial translation).

Jul. 6, 2011 International Search Report issued in International Patent Application No. PCT/IB2011/000135.

Jul. 6, 2011 Written Opinion of the International Searching Authority issued in International Patent Application No. PCT/IB2011/000135.

* cited by examiner

F I G . 4
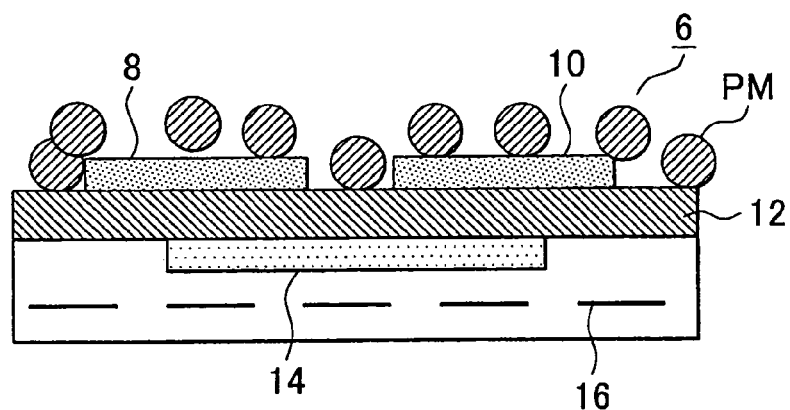
F I G . 5
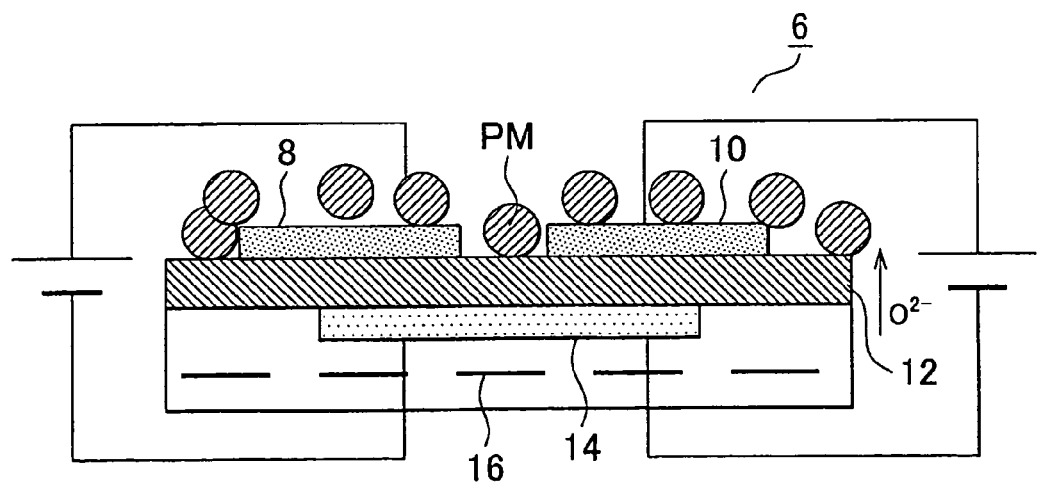

ature of
PARTICULATE MATTER DETECTING APPARATUS

BACKGROUND OF THE INVENTION

1. Field of the Invention

The invention relates to a particulate matter detecting sensor and a particulate matter detecting apparatus. More particularly, the invention relates to a particulate matter detecting sensor that is arranged in an exhaust passage of an internal combustion engine and detects an amount of particulate matter in exhaust gas, as well as to a particulate matter detecting apparatus that uses this particulate matter detecting sensor.

2. Description of the Related Art

Published Japanese Translation of PCT application No. 2006-515066 (JP-A-2006-515066), for example, describes a sensor that detects an amount of particulate matter (PM) in exhaust gas of an internal combustion engine. This sensor has electrodes arranged parallel to one another with a space therebetween. This sensor is arranged in an exhaust passage with at least a portion of the electrodes exposed to the exhaust gas. When exhaust gas passes through the exhaust passage, particulate matter in the exhaust gas accumulates on the electrodes. As a result, the impedance between the electrodes changes. The sensor described above detects this change in impedance, and detects the amount of PM accumulated between the electrodes according to this change.

Incidentally, particulate matter accumulates on the electrodes of the sensor while the PM amount is being detected. If the amount of accumulated particulate matter increases and exceeds a certain accumulation amount, the sensor will not be able to output an output value equal to or greater than that threshold value. Therefore, in order to accurately detect the PM amount, the particulate matter that has accumulated on the electrodes at a certain stage must be removed. One known way to remove particulate matter that has accumulated on a sensor is to burn off the particulate matter by heating the sensor with a heater that is built into the sensor, as described in Japanese Patent Application Publication No. 2009-144512 (JP-A-2009-144512).

When removing particulate matter that has accumulated on a sensor by burning it off, the burn-off rate is limited by the oxygen concentration in the exhaust gas. Therefore, it may take a long time to burn off the particulate matter. However, while particulate matter is being removed, the sensor is unable to be used to detect the PM amount as it is normally, so having the burn-off process for removing the particulate matter take a long time is undesirable.

Also, with the removal method that burns off the particulate matter, carbon (C) that has bonded to the electrodes of the sensor may not be sufficiently removed. Therefore, if the sensor continues to be used after burning off, i.e., removing, the particulate matter, the carbon remaining on the electrodes will gradually increase, which may cause the zero point of the sensor output to become off. If this happens, the PM amount obtained according to the sensor output will be off. Therefore, a removal method that also enables carbon that has bonded to the electrode to be sufficiently removed is desirable.

SUMMARY OF INVENTION

The invention thus provides a particulate matter detecting sensor and a particulate matter detecting apparatus that enable a process to remove particulate matter that has accumulated on an electrode to be completed in a short period of time, and to enable even carbon that has bonded to the electrode to be sufficiently removed.

A first aspect of the invention relates to a particulate matter detecting sensor. This particulate matter detecting sensor includes a pair of first electrodes that measure an amount of particulate matter in a gas; a solid electrolyte that contacts at least one of the electrodes in the pair of first electrodes; a second electrode that contacts a surface of the solid electrolyte on a side opposite the surface that the first electrodes contact; and a heating portion that heats the first electrodes and the second electrode.

According to this aspect, the second electrode is arranged such that the solid electrolyte is sandwiched between the second electrode and the first electrodes for detecting the amount of particulate matter. Thus, voltage can be applied between the first electrodes and the second electrode. As a result of applying this voltage, oxygen ions are produced at the second electrode and are pumped to the first electrodes. As a result, the oxygen ions react with the particulate matter including carbon that has bonded to the first electrodes and are then discharged. Therefore, particulate matter adhered to the first electrodes of the particulate matter detecting sensor can be reliably removed in a short period of time, and the zero point of the particulate matter detecting sensor is inhibited from becoming off, thus improving the durability of the sensor.

A second aspect of the invention relates to a particulate matter detecting apparatus that measures an amount of particulate matter in a gas by applying a predetermined voltage between a pair of first electrodes of a sensor element portion. This particulate matter detecting apparatus includes a detecting portion that detects whether more particulate matter than a reference amount has accumulated on the first electrodes; a temperature controlling portion that controls a temperature of the sensor element portion to become equal to or higher than a reference temperature when it is detected that more particulate matter than the reference amount has accumulated; and a voltage controlling portion that applies a reference voltage between the first electrodes and a second electrode arranged such that a solid electrolyte is sandwiched between the second electrode and the first electrodes, when it is detected that more particulate matter than the reference amount has accumulated.

According to this aspect, when more particulate matter than the reference amount has accumulated on the first electrodes, voltage is applied between the first electrodes and the second electrode, such that the oxygen ions produced at the second electrode are pumped to the first electrodes. As a result, the oxygen ions react with the particulate matter adhered to the first electrodes and are discharged, so particulate matter adhered to the first electrodes can be effectively removed.

In the aspect described above, the reference temperature may be 700° C., and the temperature controlling portion may control the temperature of the first electrodes to a temperature of equal to or lower than 300° C. when applying the predetermined voltage between the first electrodes and measuring the amount of particulate matter.

According to this structure, when measuring the amount of particulate matter with the first electrodes, the temperature of the electrodes is maintained at a temperature lower than 300° C., and when applying voltage between the first electrodes and the second electrode and removing particulate matter, the temperature of the electrodes is increased to 700° C. or higher. As a result, the amount of particulate matter can be measured accurately, and the particulate matter removal process can be performed quickly and sufficiently.

BRIEF DESCRIPTION OF DRAWINGS

The foregoing and further objects, features and advantages of the invention will become apparent from the following description of example embodiments with reference to the accompanying drawings, wherein like numerals are used to represent like elements and wherein:

FIG. 4 is a view of a state when a PM amount is detected by the PM sensor according to the example embodiment of the invention;

FIG. 5 is a view of a state during a PM removal process of the PM sensor according to the example embodiment of the invention;

DETAILED DESCRIPTION OF EMBODIMENTS

Figure 1:
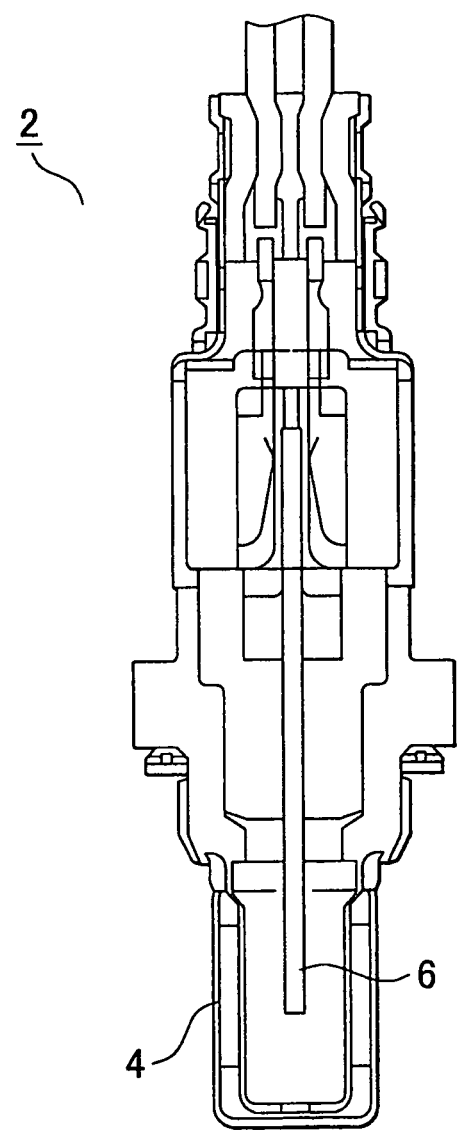
FIG. 1 is a view showing a frame format of a PM sensor according to an example embodiment of the invention.

Example embodiments of the present invention will be described in greater detail below with reference to the accompanying drawings. Incidentally, like or corresponding parts will be denoted by like reference characters and descriptions of those parts will be simplified or omitted.

Example Embodiment

Figure 2:
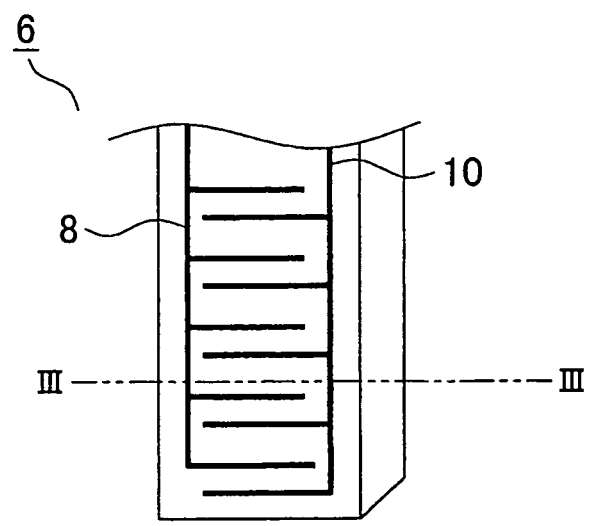
FIG. 2 is another view showing a frame format of the PM sensor according to the example embodiment of the invention.

FIGS. 1 and 2 are views showing frame formats of a particulate matter (PM) sensor according to an example embodiment of the invention, with FIG. 1 being an overall view of the PM sensor (i.e., a particulate matter detecting sensor), and FIG. 2 being an enlarged view of a portion of a sensor element portion. As shown in FIG. 1, the PM sensor 2 has a cover 4 and an element portion 6 (i.e., a sensor element portion) arranged in a space inside the cover 4. The cover 4 has a plurality of holes through which exhaust gas passes. When the PM sensor 2 is used, the cover 4 is arranged in an exhaust passage of an internal combustion engine. Exhaust gas flows into the cover 4 through the holes in the cover 4, such that the element portion 6 is exposed to the exhaust gas.

As shown in FIG. 2, the element portion 6 has a pair of electrodes (i.e., first electrodes) 8 and 10 on the surface. Hereinafter in this example embodiment, this pair of electrodes 8 and 10 will simply be referred to as "element electrodes". The element electrodes 8 and 10 of the PM sensor 2 are connected to a power supply, not shown, via a power supply circuit and the like, such that a predetermined voltage can be applied between the element electrodes 8 and 10. Detecting the output at this time using a detector, not shown, enables an amount of particulate matter (PM) in the exhaust gas that corresponds to this output to be detected.

Figure 3:
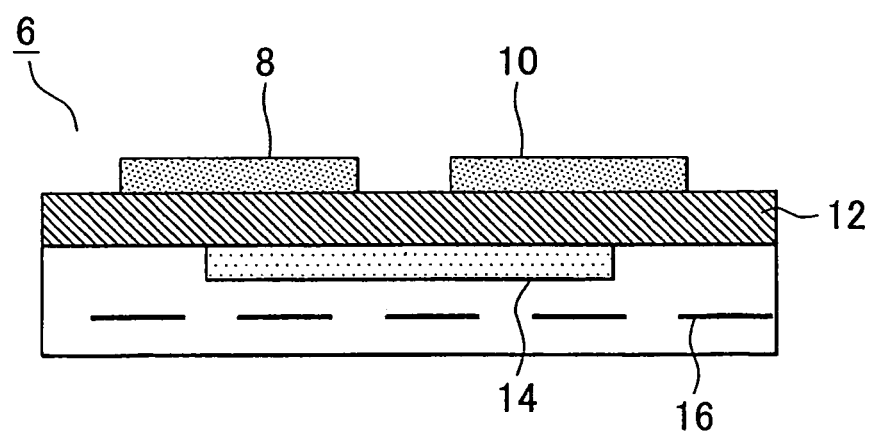
FIG. 3 is another view showing a frame format of the PM sensor according to the example embodiment of the invention.

FIG. 3 is a view showing a frame format of a section taken along line III-III in FIG. 2. The upper side of FIG. 3 corresponds to the surface side of the element portion 6 in FIG. 2. As shown in FIG. 3, a solid electrolyte 12 is arranged contacting the lower surface of the element electrodes 8 and 10. This solid electrolyte 12 has oxygen ion conductivity that transmits oxygen ions. Also, an electrode 14 (i.e., a second electrode) is arranged contacting the lower surface of the solid electrolyte 12. A heater 16 (i.e., a heating portion) is arranged below the electrode 14.

The element electrode 8 and the electrode 14 are connected to a power supply, not shown, via a power supply circuit and the like, such that voltage can be applied between the element electrode 8 and the electrode 14. Similarly, the element electrode 10 and the electrode 14 are connected to the power supply, not shown, via a power supply circuit and the like, such that voltage can be applied between the element electrode 10 and the electrode 14. The heater 16 is also connected to the power supply, not shown, via a power supply circuit and the like. The element portion 6 is heated by applying voltage to the heater 16.

The detector and the power supply and the like described above are connected to a control apparatus, not shown. The control apparatus detects the PM amount and the like according to the output of the detector and the like, calculates values according to the various outputs, and controls the voltage applied to the electrodes 8, 10, and 14, and the heater 16 with control signals to the power supply and the like.

FIG. 4 is a view of a state when the PM amount is detected by the PM sensor according to the example embodiment. The element portion 6 of the PM sensor 2 contacts the exhaust gas, so PM in the exhaust gas accumulates on the surface of the element electrodes 8 and 10, as shown in FIG. 4. The resistance of the element electrodes 8 and 10 changes according to the amount of accumulated PM. Therefore, the amount of PM in the exhaust gas of the internal combustion engine can be detected by detecting the current when a constant voltage is applied between the element electrodes 8 and 10 and calculating the resistance according to the detected current.

Incidentally, when the PM accumulated on the element electrodes 8 and 10 of the PM sensor 2 reaches a saturation state, the PM sensor 2 is unable to output any higher an output, so the PM amount is unable to be correctly measured. Therefore, PM accumulated between the element electrodes 8 and 10 must be removed before it reaches the saturation state.

One known method to remove PM involves performing a PM removal process by raising the temperature of the element portion using a heater and burning off the PM with the oxygen in the exhaust gas. However, the PM burn-off rate in this burn-off process is limited by the oxygen concentration in the exhaust gas, so it may take a considerable amount of time to burn off the PM. Also, with this burn-off process, it is difficult to completely remove carbon (C) that has bonded to the element electrodes, so the carbon may not be sufficiently removed. If the carbon on the element electrodes is not sufficiently removed, the zero point of the PM sensor output (i.e., the output immediately after the PM removal process has been performed; ideally, the output when there is no PM accumulated on the element electrodes) gradually changes and thus becomes off, so measurement error of the PM amount may increase.

Therefore, the PM removal process described below is performed in the particulates matter detecting apparatus of this example embodiment. FIG. 5 is a view of a state during a PM removal process according to the example embodiment of the invention. As described above, the PM sensor 2 is configured such that the electrode 14 is arranged below the element electrodes 8 and 10 of the element portion 6, with the solid electrolyte 12 sandwiched between the electrode 14 and the element electrodes 8 and 10. In this PM removal process, a voltage of approximately 0.5 V is applied both between the electrode 14 and the element electrode 8, and between the electrode 14 and the element electrode 10, as shown in FIG. 5. At this time, the electrode 14 becomes a negative electrode, and the element electrodes 8 and 10 become positive electrodes.

When the voltage is applied, oxygen in the exhaust gas on the electrode 14 side is broken down at the electrode 14, and this oxygen receives electrons. As a result, oxygen ions ($O^{2-}$) are produced at the electrode 14. The oxygen ions produced at the electrode 14 are pumped so that they are transmitted through the solid electrolyte 12 to the element electrode 8 and the element electrode 10. The oxygen ions that have reached the element electrode 8 and the element electrode 10 react with the carbon that bonds with the element electrodes 8 and 10, as well as with the PM accumulated on the element electrodes 8 and 10. As a result, carbon dioxide and the like is produced, which is released outside (i.e., into the exhaust passage).

In this example embodiment, the temperature of the element portion 6 (i.e., the element temperature) is maintained at 700° C. or higher by the heater 16 while the PM removal process is being performed. As a result, the oxygen ion conductance of the solid electrolyte 12 improves, such that the removal process by burning off the PM and the removal process by pumping the oxygen ions can be promoted simultaneously. As a result, the PM removal process can be completed in a short period of time.

Figure 6:
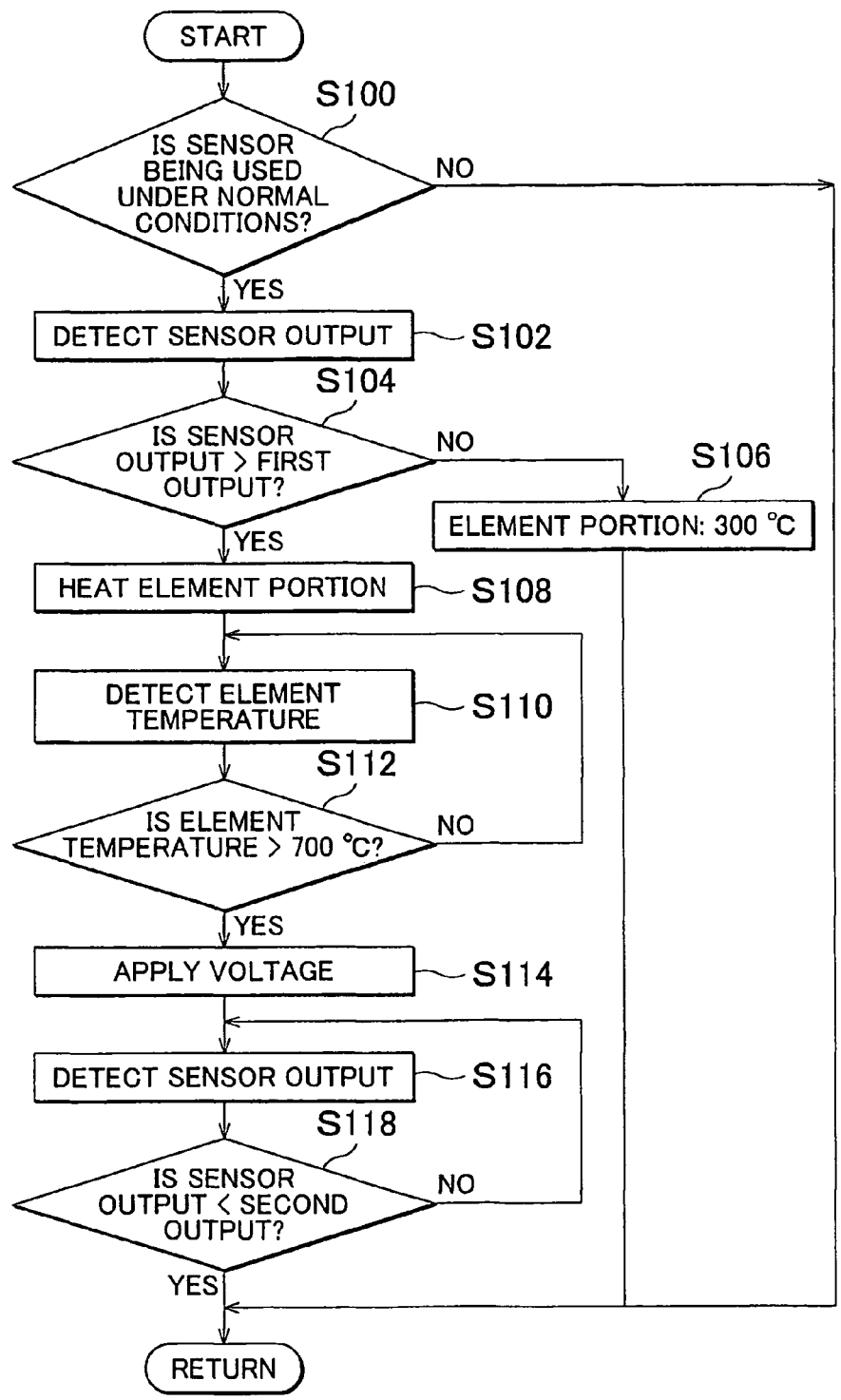
FIG. 6 is a flowchart illustrating a control routine executed by a control apparatus according to the example embodiment of the invention.

FIG. 6 is a flowchart illustrating a control routine executed by the control apparatus according to the example embodiment of the invention. In the flowchart shown in FIG. 6, it is first determined whether the sensor is being used under normal conditions (step S100). More specifically, it is determined whether the internal combustion engine and the PM sensor 2 are warmed up, for example. If it is not determined that the sensor is being used under normal conditions, this cycle of the routine ends.

If, on the other hand, it is determined in step S100 that the PM sensor 2 is being used under normal conditions, then a predetermined voltage is applied between the element electrodes 8 and 10, and the output (a current value in this case) of the PM sensor 2 is detected (step S102).

Next, it is determined whether a PM accumulated amount of the PM sensor 2 is greater than a reference amount (step S104). More specifically, this determination is made according to whether the output (i.e., the current value) of the PM sensor 2 is greater than a first output corresponding to the reference amount, for example. The reference amount is a value near a threshold value at which, if any more PM accumulates, the PM amount is unable to be correctly detected. An output corresponding to the reference amount is stored beforehand in the control apparatus.

If it is not determined in step S104 that the PM sensor output is greater than the first output, then it is determined that the PM removal process is not necessary at the current stage, so the temperature of the element portion 6 is maintained at a temperature of equal to or less than 300° C. (step S106) and this cycle of the routine ends.

If, on the other hand, it is determined in step S104 that the PM sensor output, is greater than the first output, then the PM removal process starts. Here, the temperature of the element portion 6 is first increased (step S108). More specifically, the element portion 6 is heated by voltage applied to the heater 16 being controlled according to a control signal from the control apparatus.

Next, the element temperature is detected (step S110), and it is determined whether the element temperature is equal to or greater than 700° C. (step S112). If it is not determined that the element temperature is equal to or greater than 700° C., then heating by the heater 16 is continued and the element temperature detection (step S110) and the element temperature determination (step S112) are repeated until the element temperature becomes equal to or greater than 700° C.

If, on the other hand, it is determined in step S112 that the element temperature is equal to or greater than 700° C., then a reference voltage is applied between the element electrode 8 and the electrode 14, as well as between the element electrode 10 and the electrode 14 (step S114). Here, a voltage of 0.5 V is applied as the reference voltage by a control signal from the control apparatus. Accordingly, oxygen ions are produced at the electrode 14, and the produced oxygen ions are pumped through the solid electrolyte 12 and reach the element electrodes 8 and 10. As a result, the oxygen ions react with the PM (including carbon bonded to the element electrodes 8 and 10) adhered to the element electrodes 8 and 10, such that the PM is removed from the element electrodes 8 and 10.

Next, the output (i.e., the current value) of the PM sensor 2 is detected (step S116) and it is determined whether the sensor output is less than a second output (step S118). This second output is a value that is set in advance to an output near the zero point of the PM sensor 2, and is stored in the control apparatus. If it is not determined that the sensor output is less than the second output, then the detection of the sensor output (step S116) and the determination of the sensor output (step S118) are repeated while voltage continues to be applied.

If, on the other hand, it is determined that the sensor output is less than the second output in step S118, then it is determined that the removal of PM including C adhered to the surface of the element electrodes 8 and 10 is complete and the output is near the zero point, so this cycle of the routine ends.

Figure 7:
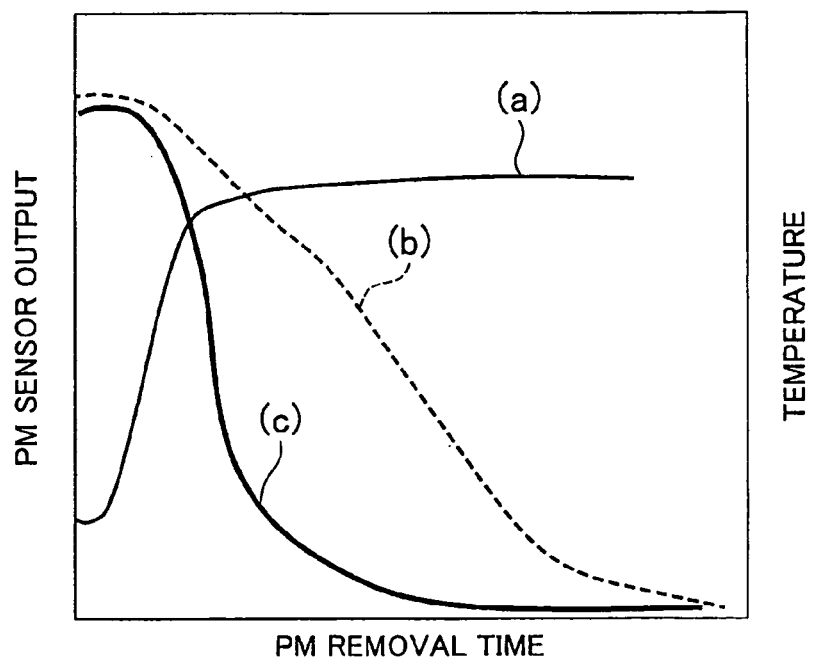
FIG. 7 is a graph comparing the relationship between the PM removal time and the sensor output with the PM sensor according to the example embodiment of the invention with the relationship between the PM removal time and the sensor output with a PM sensor according to related art.

FIG. 7 is a graph comparing the relationship between the PM removal time and the PM sensor output with PM removal according to related art, with the relationship between the PM removal time and the PM sensor output when the PM removal process according to this example embodiment is performed. The horizontal axis in FIG. 7 represents the PM removal time, and the vertical axes represent the PM sensor output (i.e., the current value) and the temperature. Also in FIG. 7, the thin solid line (a) represents the element temperature, the broken line (b) represents a case in which a PM removal process according to related art is performed, and the solid line (c) represents a case in which the PM removal process according to this example embodiment is performed.

From FIG. 7, it is evident that, with the removal process of this example embodiment (i.e., the solid line (c)), the output of the PM sensor 2 reliably recovers within a short period of time compared with the removal process according to the related art (i.e., the broken line (b)). That is, with the removal process according to this example embodiment, the PM removal process is able to be completed in a short period of time.

Figure 8:
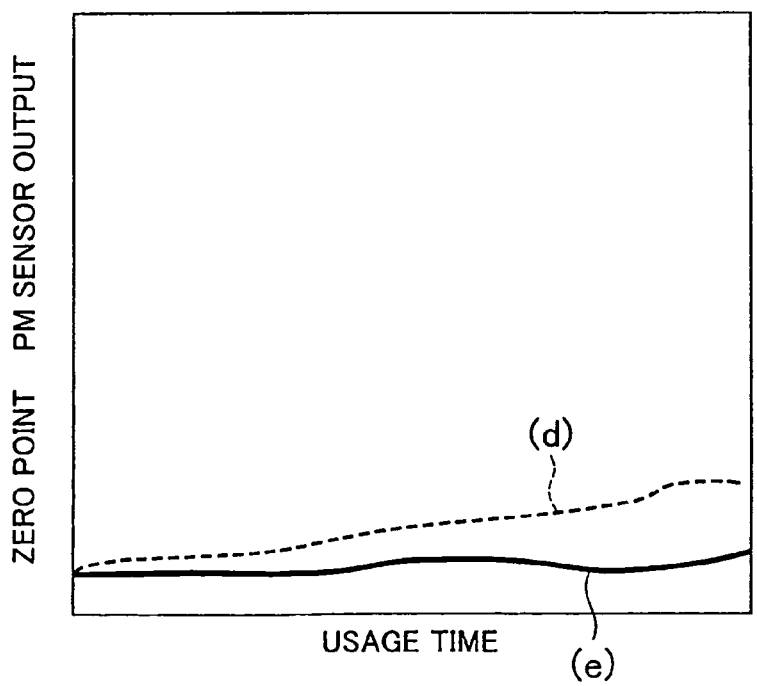
FIG. 8 is a graph comparing the relationship between the usage time and the sensor zero point with the PM sensor according to the example embodiment of the invention with the relationship between the usage time and the sensor zero point with the PM sensor according to the related art.

FIG. 8 is a graph showing the change over time in the output zero point of the PM sensor 2 when a PM removal process according to related art is performed and when the PM removal process according to this example embodiment is performed. In FIG. 8, the horizontal axis represents the usage time of the PM sensor and the vertical axis represents the sensor output zero point. Also, in FIG. 8, the broken line (d) represents a case in which the PM removal process according to the related art is performed, and the solid line (e)

represents a case in which the PM removal process according to this example embodiment is performed.

From FIG. 8, it is evident that, with the PM removal process according to this example embodiment (i.e., the solid line (e)), the change in the zero point of the PM sensor 2 is able to be kept smaller than it is with the PM removal process according to the related art (i.e., the broken line (d)). That is, the PM removal process of this example embodiment enables the durability of the PM sensor 2 to be improved.

Incidentally, this example embodiment describes a case in which a single electrode 14 for pumping oxygen ions is provided as a common electrode for the element electrodes 8 and 10. However, the invention is not limited to this. That is, a separate electrode may be provided for each of the element electrodes 8 and 10.

Also, the applied voltage and the temperature during the PM removal process described in this example embodiment are not intended to limit the invention. These values may be set appropriately according to the properties of the PM sensor 2 and the usage environment and the like.

Incidentally, in this example embodiment, the detecting portion of the invention is realized by the execution of step S104, the temperature controlling portion of the invention is realized by the execution of step S106 or steps S108 to S112, and the voltage controlling portion of the invention is realized by the execution of step S114.

Incidentally, the invention is not limited to the numbers used to indicate number of elements, quantities, amounts, and ranges and the like referred to in this example embodiment. Similarly, the structure and the like of the invention are not limited to that described in this example embodiment.

What is claimed is:

1. A particulate matter detecting apparatus that measures an amount of particulate matter in a gas comprising:
    a particulate matter sensor configured to measure the amount of particulate matter in the gas, the particulate matter sensor comprising:
        a solid electrolyte that has oxygen ion conductivity and that transmits oxygen ions;
        a pair of first electrodes, the pair of first electrodes arranged to contact one surface of the solid electrolyte, wherein a predetermined voltage is capable of being applied between the pair of first electrodes so as to detect the amount of particulate matter accumulated on the pair of first electrodes; and
        a second electrode that contacts another surface of the solid electrolyte on a side opposite the one surface that the first electrodes contact, the second electrode arranged such that the solid electrolyte is sandwiched between the second electrode and the first electrodes;
    a heater configured to heat the first es and the second electrode;
    a detector configured to detect the output of the particulate matter sensor to detect amount of particulate matter on the first electrodes; and
    a controller configured to:
        determine whether the amount of particulate matter on the first electrodes is more than a reference amount;
        control a temperature of the particulate matter sensor to become equal to or higher than a reference temperature when the controller determines that more particulate matter than the reference amount has accumulated on the first electrodes; and
        control the application of a reference voltage between the first electrodes and the second electrode from a power supply when the controller determines that more particulate matter than the reference amount has accumulated on the first electrodes, wherein:
    when the first electrodes and the second electrode are heated, the first electrodes are set as positive electrodes and the second electrode is set as a negative electrode, and the power supply applies the reference voltage between the first electrodes and the second electrode; and
    when the power supply applies the reference voltage between the first electrodes and the second electrode, oxygen ions are produced at the second electrode and the oxygen ions produced are pumped through the solid electrolyte to reach the first electrodes.

2. The particulate matter detecting apparatus according to claim 1, wherein the reference temperature is 700° C., and the controller is configured to control a temperature of the first electrodes to a temperature equal to or lower than 300° C. when applying the predetermined voltage between the first electrodes and measuring the amount of particulate matter.

3. The particulate matter detecting apparatus according to claim 1, wherein the oxygen ions produced at the second electrode and pumped to the first electrodes react with the particulate matter including carbon adhered to the first electrodes to remove the particulate matter adhered to the first electrodes.

* * * * *